(12) United States Patent
Asensio Dominguez et al.

(10) Patent No.: US 6,642,364 B2
(45) Date of Patent: Nov. 4, 2003

(54) PROCESS TO OBTAIN CLARITHROMYCIN

(75) Inventors: Ramón Asensio Dominguez, Aranjuez (ES); Maria del Carmen Cruzado Rodriguez, Aranjuez (ES); Luis Ángel Diaz Tejo, Aranjuez (ES); Rosa Nomen Ribé, Barcelona (ES); Julià Sempere Cebrián, Barcelona (ES); José Ignacio Borrell Bilbao, Barcelona (ES)

(73) Assignee: Ercros Industrial, S.A., Barcelona (ES)

( * ) Notice: Subject to any disclaimer, the term of this patent is extended or adjusted under 35 U.S.C. 154(b) by 0 days.

(21) Appl. No.: 10/180,127

(22) Filed: Jun. 27, 2002

(65) Prior Publication Data

US 2003/0023053 A1 Jan. 30, 2003

(30) Foreign Application Priority Data

Jul. 5, 2001 (ES) .......................................... 200101562

(51) Int. Cl.$^7$ ............................................... C07H 17/08
(52) U.S. Cl. ............................ 536/7.2; 536/7.3; 536/7.4
(58) Field of Search ............................ 536/7.2, 7.4, 7.3

(56) References Cited

U.S. PATENT DOCUMENTS 4,990,602 A * 2/1991 Morimoto et al. ........... 536/7.4

FOREIGN PATENT DOCUMENTS

WO     WO 99/28333    * 6/1999   ......... C07H/17/08

OTHER PUBLICATIONS

Watanabe, Y. et al "Chemical Modifications of Erythromycins XIL. A Facile Synthesis of Clarithromycin via 2'–silylethers of Erythromycin A Derivatives", The Journal of Antibiotics, 1993, 46(7), 1163–1167.*

* cited by examiner

Primary Examiner—James O. Wilson
Assistant Examiner—Ganapathy Krishnan
(74) Attorney, Agent, or Firm—Sughrue Mion, PLLC

(57) ABSTRACT

This process is intended to obtain clarithromycin. According to the process, it starts from the erythromycin A 9-oxime hydrochloride, which is transformed into clarithromycin by means of a synthetic sequence in which an acetal of the 9-oxime is initially formed. The use of the oxime hydrochloride permits that only the use of catalytic amounts of pyridine salts are necessary to favor the reaction. Next, the hydroxyls in positions 2' and 4" are protected with a silylating agent and the hydroxyl in position 6 is methylated; all this without the isolation of any reaction intermediate being necessary. Finally, the acetal and 2' and 4" silanes unprotection, followed by the deoximation yields clarithromycin with a high yield and a form which is easily applicable industrially.

4 Claims, No Drawings

PROCESS TO OBTAIN CLARITHROMYCIN

BACKGROUND

Clarithromycin is the USAN generic name of the 6-O-methylerythromycin A (formula I). It is a compound derived from erythromycin A which, like this, belongs to the macrolide antibiotics group. The structural difference between both compounds lies in the methylation of the hydroxyl at position 6 of the macrolactone. This modification avoids the inactivation that the erythromycin A undergoes due to the gastric acids and the subsequent reduction in absorption (Nakagawa, Y., Itai, S., Yoshida, T., Nagai, T., *Chem. Pharm. Bull.*, 1992, 40, 725–728).

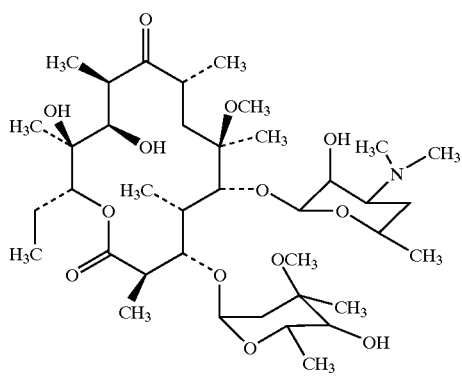

I

This compound was first disclosed by Y. Watanabe et al. (Taisho Pharmaceutical Co.) in the patent document EP 41.355 (and in the equivalent document U.S. Pat. No. 4,331,803). The process disclosed in said document starts from N-de-methylerythromycin A and protects the 2'-hydroxyl and the de-methylamine group in the form of a benzyloxycarbonyl derivative. Next, the 6-hydroxyl is methylated with methyl iodide and the 2'-hydroxyl and the de-methylamine group becomes unprotected by hydrogenolysis. Finally, the amine group is methylated with formaldehyde in a reductive methylation.

Since the publication of said patent document other alternative methods have been developed to obtain clarithromycin starting from erythromycin A. The common characteristic of said methods is to previously obtain the erythromycin A 9-oxime, which is protected together with the 2'-hydroxyl to subsequently proceed with the 6-hydroxyl methylation. These processes end with the unprotection of the oxime and the 2'-hydroxyl followed by the elimination of the oxime group by means of a NaHSO$_3$ treatment. Said alternative methods differ in the protective group used to block the oxime group and the 2'-hydroxyl. Thus, alkoxycarbonyl (EP 158.467) and benzyl or substituted benzyl groups (EP 195.960) have been used to protect both groups. A benzyl or substituted benzyl group and the 2'-hydroxyl have also blocked the oxime with a benzyloxycarbonyl group (EP 180.415) or with a trimethylsilyl group (EP 260.938).

Subsequently, the use of a mixed acetal to protect the oxime group has been disclosed (U.S. Pat. No. 4,990,602), followed by the protection of the 2'-hydroxyl and 4"-hydroxyl groups using trimethylsilylated derivatives and the 6-hydroxyl methylation with methyl iodide. The subsequent unprotection of the silyl groups and the acetal by means of a treatment with formic acid and elimination of the oxime group with Na$_2$S$_2$O$_5$ would permit obtaining the clarithromycin, although said stages are not disclosed in said patent document U.S. Pat. No. 4,990,602.

In an example of said patent document U.S. Pat. No. 4,990,602, one starts with the erythromycin A oxime, which is treated in a methylene chloride solution with the diisopropyl acetal of the ciclohexanone in the presence of pyridine hydrochloride to obtain the mixed acetal of said oxime. Next, the 2'-hydroxyl and 4"-hydroxyl groups are protected by means of a treatment with trimethylsilylimidazole and chlortrimethylsilane in methylene chloride and finally the 6-hydroxyl group is methylated with methyl iodide and potassium hydroxide in a 1:1 mixture of dimethyl-sulfoxide and tetrahydrofuran to obtain the erythromycin A 2',4"-bis (trimethylsilyl)-6-O-methyl-9-[O-isopropoxy-cyclohexyl] oxime, which is transformed into the clarithromycin as noted above.

DESCRIPTION OF THE INVENTION

The object of the present invention is a new process that permits clarithromycin synthesis in a simple manner and with a high yield characterized by:

Starting from the erythromycin A oxime hydrochloride, which is transformed into clarithromycin by means of a synthetic sequence which in its first three stages avoids having to isolate the intermediate products, which facilitates its industrial applicability.

Simplification of the number of solvents used in the first three stages of the synthesis.

The use of catalytic amounts (<1% in weight) of pyridine salt in the synthesis reaction of the mixed acetal of the oxime.

All the clarithromycin synthesis processes that achieve acceptable yields start from the erythromycin A 9-oxime. In the known 9-oxime synthesis procedures (see documents GB 110.0504, EP 342.990), it is passed through a salt, that can be isolated or not, before obtaining the oxime. During the investigation it has been found that the use of the erythromycin A 9-oxime hydrochloride permits advantageously performing the clarithromycin synthesis when, in its first synthesis stage, the oxime group is protected by a 1,1-diisopropoxycyclohexane to form a mixed acetal.

It has been found that the use of the erythromycin A 9-oxime hydrochloride permits, surprisingly, reducing, to a great extent, the amount of acid catalyst needed to perform the protection reaction of the hydroxyl group of the oxime.

The process, according to the invention, starts with the use of the erythromycin A 9-oxime hydrochloride, which is made to react with the diisopropylic acetal of the cyclohexanone, using methylene chloride as a solvent, to form a mixed acetal. The use of the oxime hydrochloride avoids the addition of large amounts of pyridine salt, being able to use a catalytic ratio of pyridine salt with respect to the oxime hydrochloride in the order of 1:100 towards the 1:5 ratio disclosed in the examples of the patent document U.S. Pat. No. 4,990,602. It has also been observed that it is not necessary to use the pyridine hydrochloride disclosed in this document; in its place pyridine hydrobromide can be used, which is an equally efficient substitute, cheaper and more easily manipulated, as it is much less hygroscopic than the pyridine hydrochloride.

After the mixed acetal forming reaction and without its isolation being necessary, the silylation of the 2' and 4" position hydroxyls at low temperature is proceeded with, by means of the addition of a silylation reactive, giving rise to the erythromycin A 2',4"-bis (trimethylsilyl)-9-[O- isopropoxy cyclohexyl] oxime. The reaction takes place in the same solvent used in the former stage: methylene chloride. The silylation reactive is obtained by a reaction between hexamethyldisilazane and imidazole in the presence of sulphuric acid, followed by the addition of chlortrimethylsilane.

In the following methylation reaction, dimethylsulfoxide, methyl iodide and potassium hydroxide are added to the erythromycin A 2',4"-bis(trimethylsilyl)-9-[O-isopropoxycyclo-hexyl]oxime solution, which is not necessary to isolate either, to synthesize the erythromycin A 2',4"-bis(trimethylsilyl)-6-O-methyl-9-[O-isopropoxy cyclohexyl]oxime. To continue with the reactions sequence, the dimethylsulfoxide is extracted with water, the aforementioned intermediate remaining dissolved in methylene chloride. Next, a change of solvent is carried out, by means of distillation, leaving the intermediate erythromycin A 2',4"-bis(trimethylsilyl)-6-O-methyl-9-[O-isopropoxycyclo-hexyl]oxime dissolved in methanol.

In the next stage the unprotection of the silyl groups and the acetal takes place, in a methanol/water solution and in the presence of formic acid, to obtain the clarithromycin 9-oxime, which precipitates at a basic pH and is recovered by filtration. Finally, this intermediate is dissolved in methanol and is treated with aqueous sodium metabisulphite at a pH of 4.5–5, adjusted with formic acid, to obtain clarithromycin, which is subsequently crystallized by means of adjustment to a basic pH.

The yield attained with this method is very high, being able to obtain a 70% yield from the oxime hydrochloride to the clarithromycin, which, if necessary, can be recrystallized by means of standard methods.

The starting material, i.e. erythromycin A 9-oxime hydrochloride can be obtained as is disclosed in the previous stage, explained further on, or rather following other methods disclosed in the bibliography, such as in the first part of example 3 of the patent U.S. Pat. No. 5,274,085.

Example of Obtaining Clarithromycin According to the Invention's Process

Previous Stage.—Synthesis of the Erythromycin A 9-oxime Hydrochloride 28 ml of methanol and 15 g of erythromycin A are introduced in the reactor under stirring. Next, 7.6 g of imidazole and 7.1 g of hydroxylamine hydrochloride are added. The mixture is heated to reflux and this is maintained for 8 h. The mixture is later cooled to 0° C. and the solid that appears is recovered by filtration. The solid obtained is suspended in 30 ml of water which is stirred for 15 minutes. The solid obtained is recovered by filtration and is vacuum dried at 50° C. for 12 h. 12.5 g of erythromycin A 9-oxime hydrochloride are obtained.

Stage a.—Synthesis of the Mixed Acetal 9.4 g of erythromycin A 9-oxime hydrochloride and 55 ml of $CH_2Cl_2$ are introduced in the reactor, and the stirring is turned on. 0.09 g of pyridine hydrobromide is introduced and the solution is maintained at 15° C. 8.4 g of diisopropoxycyclohexane are added. The stirring is maintained at 15–20° C. for 1.5 h. Once the reaction has ended, the solution is washed with 28 ml of 5% NaOH and with 28 ml of a saturated NaCl solution. Finally, 38 ml de $CH_2Cl_2$ is added to the organic phase and distilled until a volume of 48 ml of $CH_2Cl_2$ is obtained. Approximately 50 ml of erythromycin A 9-[O-isopropoxycyclohexyl]oxime solution in $CH_2Cl_2$ is obtained, ready to be used in the following stage.

Stage b.—Preparation of the Silylation Agent 20 g of hexamethyldisilazane and 15.8 g of imidazole are introduced in the reactor and the stirring is turned on. 0.01 ml of concentrated sulphuric acid is slowly added. It is heated to 130–140° C. and is maintained at this temperature for 2 h. The solution is cooled to 20–25° C. and 84 ml of $CH_2Cl_2$ is introduced and, then, 26 g of chlortrimethylsilane. A white suspension is formed that is ready to be used in the silylation reaction.

Stage c.—Silylation Reaction

The solution of mixed acetal in $CH_2Cl_2$ obtained in Stage a is cooled to −5–0° C. Once the temperature has been reached, the silylation agent solution obtained in Stage b is slowly introduced. The stirring is maintained at the same temperature for 60'. Once the reaction has ended, two washes are carried out with 19 ml of water and 19 ml of saturated NaCl solution. Finally, 25 ml of methylene chloride is added and is distilled until a final volume of 62 ml of erythromycin A 2',4"-bis(trimethylsilyl)-9-[O-isopropoxycyclohexyl]oxime solution is obtained.

Stage d.—Methylation Reaction 56 ml of dimethylsulfoxide is introduced in the reactor containing the solution from Stage c. The solution is cooled to 0–5° C. Once the indicated temperature is reached, 2.8 g of methyl iodide and 1.1 g of 89% potassium hydroxide powder are added. The stirring is maintained at 0–5° C. for 3h. Once the reaction has finished, 1.6 g of triethylamine are added at 0–5° C., the temperature is allowed to rise to 20–25° C. and, once reached, stirring is maintained for 45 min. Next, the solution is washed with 56 ml of water and 44 ml of saturated sodium chloride solution. Finally, the methylene chloride organic phase is distilled until an oily solution is obtained. Next, 72 ml de methanol is introduced and 20 ml of solution is distilled to eliminate the methylene chloride. Thus, a methanol solution of erythromycin A 2',4"-bis(trimethylsilyl)-6-O-methyl-9-[O-isopropoxycyclohexyl]oxime is obtained.

Stage e.—Unprotection Reaction 52 ml of water is introduced in the reactor with the methanolic solution obtained in Stage d, and pH is adjusted to 3–3.5 with formic acid (85%). The solution is heated to 35–40° C. for 3–5 h. Once the reaction has finished, 52 ml of water is introduced. The clarithromycin oxime is obtained by adding NaOH to a pH of 9.5–10. The solid obtained is recovered by filtration.

Stage f.—Deoximation Reaction

The solid obtained in Stage e is dissolved in 38 ml of methanol. 38 ml of water and 3.8 g of sodium metabisulphite are added to the solution obtained. The pH is adjusted to 4.5–5 with formic acid (85%). It is heated to reflux for 2–4 h. Once the reaction is finished, it is cooled to 20–25° C. and 56 ml of water is introduced. At the same temperature, the pH is adjusted to 10 with sodium hydroxide until the crystallization of the clarithromycin is achieved, which is recovered by filtration. 6.3 g of clarithromycin are obtained, which is recrystallized from ethanol to obtain the final clarithromycin. It is vacuum dried at 90–95° C. for 24 h. In this manner, obtaining the clarithromycin crystal form II is guaranteed (according to the terminology used in the description of the patent documents WO 98/04573 and WO 98/04574), that is habitually used in commercial formulations.

What is claimed is:

1. A process for producing clarithromycin comprising the steps of:

(a) reacting erythromycin A 9-oxime hydrochloride with 1,1-diisopropoxycyclohexane in the presence of a catalytic amount of a pyridine salt, in methylene chloride as a solvent, so as to obtain a mixed acetal;

(b) reacting hexamethyldisilazane and imidazole in the presence of sulfuric acid, and thereafter adding chlorotrimethysilane in methylene chloride as a solvent, so as to obtain a silylation agent;

(c) reacting the resulting mixed acetal of step (a) with the resulting silylation agent of step (b) in methylene chloride as a solvent, so as to obtain erythromycin A 2',4"-bis(trimethylsilyl)-9-[O-isopropoxycyclohexyl]oxime;

(d) reacting the resulting erythromycin A 2',4"-bis(trimethylsilyl)-9-[O-isopropoxycyclohexyl]oxime of step (c) with methyl iodide and potassium hydroxide in methylene chloride and dimethylsulfoxide as solvents, so as to obtain erythromycin A 2',4"-bis(trimethylsilyl)-6-O-methyl-9-[O-isopropoxycyclohexyl]oxime;

(e) deprotecting the resulting erythromycin A 2',4"-bis(trimethylsilyl)-6-O-methyl-9-[O-isopropoxycyclohexyl]oxime obtained in step (d) in a solution of methanol, water and 85% formic acid, so as to obtain clarithromycin oxime; and (f) deoximating the resulting clarithromycin oxime of step (e) with aqueous sodium metabisulfite so as to obtain clarithromycin.

2. The process of claim 1, wherein steps (a), (b), (c) and (d) are carried out without isolating reaction intermediates.

3. The process of claim 1, wherein in step (a) said pyridine salt is pyridine hydrobromide.

4. The process of claim 1, wherein said pyridine salt is pyridine hydrobromide, which is employed at a molar ratio of about 0.04 to 0.05 to said erythromycin A 9-oxime hydrochloride.

* * * * *